United States Patent [19]

Durfee

[11] Patent Number: 5,246,703
[45] Date of Patent: Sep. 21, 1993

[54] SILOXY-FUNCTIONAL CYCLOPOLYSILOXANES

[75] Inventor: Loren D. Durfee, Midland, Mich.

[73] Assignee: Dow Corning Corporation, Midland, Mich.

[21] Appl. No.: 813,721

[22] Filed: Dec. 27, 1991

[51] Int. Cl.$^5$ .................. A61K 31/695; A61K 7/06
[52] U.S. Cl. ................................ 424/401; 424/70; 556/460
[58] Field of Search .................. 424/401, 70, 71; 556/460

[56] References Cited

U.S. PATENT DOCUMENTS

| | | | |
|---|---|---|---|
| 4,497,943 | 2/1985 | Takago et al. | 556/460 |
| 4,574,082 | 3/1986 | Tietjen | 424/63 |
| 5,086,146 | 2/1992 | Liles et al. | 556/460 |
| 5,089,250 | 2/1992 | Forestier et al. | 424/401 |
| 5,104,643 | 4/1992 | Grollier | 424/70 |

OTHER PUBLICATIONS

Chemical Abstracts, vol. 116, No. 10, Item. No. 85928v.
Chemical Abstracts, vol. 112, No. 22, Item. No. 204466x.

Primary Examiner—Thurman K. Page
Assistant Examiner—Raj Bawa
Attorney, Agent, or Firm—Alexander Weitz

[57] ABSTRACT

A cyclopolysiloxane having the general structure

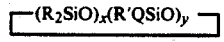

wherein Q is a monovalent siloxane moiety selected from the group consisting of the structure $(R_3SiO)_2SiR—A—$ and the structure $GR_2SiOSiR_2—A'—$, in which A is a divalent hydrocarbon group having 4 to 14 carbon atoms and A' is a divalent hydrocarbon group having 2 to 18 carbon atoms, each R' group and each G group is independently selected from the group consisting of an alkyl radical having 1 to 30 carbon atoms, a phenyl radical, an arylalkyl group and a halogenated alkyl radical having 3 to 6 carbon atoms, each R is independently selected from the group consisting of an alkyl radical having 1 to 30 carbon atoms. a phenyl radical, an arylalkyl group, a halogenated alkyl radical having 3 to 6 carbon atoms and hydrogen, and x and y are each integers, with the proviso that (x+y) is an integer having a value of 4 to 6 inclusive and y is at least 1.

21 Claims, No Drawings

SILOXY-FUNCTIONAL CYCLOPOLYSILOXANES

FIELD OF THE INVENTION

The present invention relates to cyclic siloxanes and particularly to cyclopolysiloxanes having from four to six silicon atoms which have siloxy moieties attached thereto through hydrocarbon connecting groups.

BACKGROUND OF THE INVENTION

Many of today's formulated products which are purchased by industry and consumer alike rely on the inclusion of linear or cyclic organosiloxanes, either as a main ingredient or as an additive, to achieve some particular advantage over comparable products which do not comprise such silicone components. Arts as diverse as those concerned with antiperspirants, skin care compositions, cosmetics, hair care formulations, hydraulic fluids, waterproofing agents, lubricants, paint additives and mold release agents, inter alia, derive benefit by such modification. Thus, for example, the use of dialkylcyclosiloxanes of various types is well known in the above applications, alkylmethylcyclopolysiloxanes being the most common. When the alkyl groups of the latter cyclic siloxanes are short (e.g., less than about 12 carbon atoms), the compounds are typically low viscosity liquids at ordinary temperatures, while solid, waxlike consistency is often observed when the alkyl groups have more than about 12 carbon atoms. In certain applications, however, it is desirable to have a relatively long alkyl chain attached to the silicon atoms of the cyclopolysiloxane structure (e.g., to impart improved lubricity or organic compatibility thereto) while at the same time maintaining the ease of handling associated with a fluid, rather than a waxlike component.

SUMMARY OF THE INVENTION

Applicant has now discovered a class of siloxy-functional cyclopolysiloxanes which fulfills the above mentioned need. These cyclic siloxanes typically exhibit considerably lower melting points than the corresponding organo-functional cyclopolysiloxanes of the prior art having hydrocarbon substitution of comparable length. The compounds of the invention thus offer the skilled artisan an added measure of flexibility in the formulation, development and design of various products of the type mentioned above. The present invention therefore relates to a cyclic siloxane having the general structure

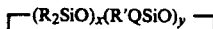

wherein Q is a monovalent siloxane moiety selected from the group consisting of the structure $(R_3SiO)_2SiR-A-$ and the structure $GR_2SiOSiR_2-A'-$, in which A is a divalent hydrocarbon group having 4 to 14 carbon atoms and A' is a divalent hydrocarbon group having 2 to 18 carbon atoms, each R' group and each G group is independently selected from the group consisting of an alkyl radical having 1 to 30 carbon atoms, a phenyl radical, an arylalkyl group and a halogenated alkyl radical having 3 to 6 carbon atoms, each R is independently selected from the group consisting of alkyl radicals having 1 to 30 carbon atoms, a phenyl radical, an arylalkyl group, a halogenated alkyl radical having 3 to 6 carbon atoms and hydrogen, and x and y are each integers, with the proviso that (x+y) is an integer having a value of 4 to 6 inclusive and y is at least 1.

DETAILED DESCRIPTION OF THE INVENTION

The cyclic siloxanes of the present invention have the general structure

wherein Q is a monovalent siloxane moiety selected from the structure $(R_3SiO)_2SiR-A-$ or the structure $GR_2SiOSiR_2-A-$, in which A is a divalent linear or branched hydrocarbon connecting group having 4 to 14 carbon atoms and A' is a divalent linear or branched hydrocarbon connecting group having 2 to 18 carbon atoms. In the above formulas each R' group and each G group is independently selected from the group consisting of an alkyl radical having 1 to 30 carbon atoms, a phenyl radical, an arylalkyl group, such as styryl or alpha-methylstyryl, and a halogenated alkyl radical having 3 to 6 carbon atoms, such as trifluoropropyl. It is preferred that each R' is an alkyl radical having 1 to 3 carbon atoms, most preferably a methyl radical. The group R in formula (I) may likewise be selected from the group consisting of an alkyl radical having 1 to 30 carbon atoms, a phenyl radical, an arylalkyl group and a halogenated alkyl radical having 3 to 6 carbon atoms, but may also be hydrogen. Again, it is preferred that R is an alkyl radical having 1 to 3 carbon atoms, most preferably a methyl radical. The cyclic siloxanes of the invention have four, five or six silicon atoms in their rings such that x and y shown in formula (I) are each integers, while the sum (x+y) is an integer having a value of 4 to 6 inclusive with the further proviso that y is at least 1. Both copolymeric cyclic species and homopolymeric cyclic species (i.e., x=0) are contemplated herein. Preferably, x=0 and y=4.

The above mentioned connecting group A is preferably a linear hydrocarbon group having the formula $-(CH_2)_n-$, in which n is 6 to 14. Likewise, the connecting group A' is preferably a linear hydrocarbon group having the formula $-(CH_2)_m-$, in which m is 2 (i.e., a dimethylene group). Above described group G is preferably a linear alkyl radical having 5 to 20 carbon atoms.

Specific examples of the cyclic siloxanes of the invention include such compounds as those represented by the following formulas:

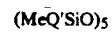

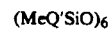

wherein Me hereinafter denotes a methyl radical and Q' has one of the following structures

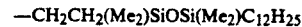

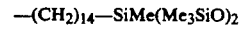

A preferred method for preparing the cyclic siloxanes wherein Q is the group (R₃SiO)₂SiR—A— comprises the steps of first forming a terminally-unsaturated intermediate by reacting an SiH-functional siloxane with an excess of, e.g., a linear diene according to the equation $$(R_3SiO)_2Si(R)H + CH_2=CH(CH_2)_kCH=CH_2 \rightarrow (R_3SiO)_2SiRCH_2CH_2(CH_2)_kCH=CH_2 \quad (II)$$

wherein k is an integer having a value of 0 to 10, inclusive, so as to comport with the previous definition of group A. The above intermediate is purified by removing the excess diene and then reacting it with a organohydrogencyclopolysiloxane, as shown in equation (III):

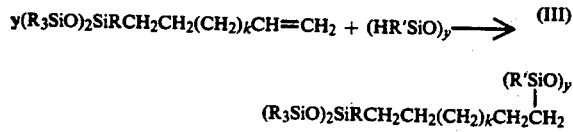

wherein R, R' and k and y have their previously defined meanings. It will, of course, be recognized by those skilled in the art that, although the equations (II) and (III) illustrate preparation of a homopolymeric cyclic compound (i.e., wherein x=0), the use of a mixed organohydrogencyclopolysiloxane, which additionally contains (R₂SiO) units in its ring, would result in the generic structure of the invention when similarly reacted with the above described intermediate. The above hydrosilation reactions are well known in the art and are typically conducted at elevated temperatures, such as 50° C. to 180° C., using platinum catalysts, such as platinum on carbon, chloroplatinic acid or various platinum/siloxane complexes described in the patent and scientific literature.

In a like manner, the preferred method for preparing the cyclic siloxanes wherein Q is the group GR₂Si-OSiR₂—A'— comprises the steps of first forming a siloxane intermediate having a terminal SiH group by reacting an excess of an alpha-omega SiH-functional siloxane with, e.g., a terminally unsaturated alkene according to the equation $$HR_2SiOSiR_2H + CH_2=CH-G' \rightarrow HR_2SiOSiR_2CH_2CH_2-G' \quad (IV)$$

The above intermediate is purified by removal of excess dihydrido siloxane and it is then reacted with an organoalkenylcyclopolysiloxane, as shown in equation (V). In equation (IV), group G has been redefined as —CH₂CH₂—G' and this reaction is thus illustrative of the case wherein above defined group G is an alkyl chain. The skilled artisan will of course recognize that when another group G of the invention is selected (e.g., a phenyl radical), the reaction represented by equation (IV) may be eliminated and the appropriate disiloxane (e.g., HR₂SiOSiR₂PH, wherein Ph denotes a phenyl radical) is reacted with the cyclopolysiloxane shown in equation (V).

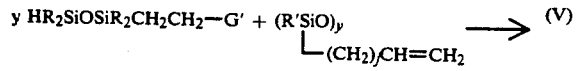

wherein j is an integer having a value of 0 to 16, inclusive, so as to comport with the previous definition of group A', while y, R and R' have their previously defined meanings. Again, the general structure of the invention may be obtained by the use of a mixed organoalkenylcyclopolysiloxane in carrying out reaction (V). Reactions represented by equations (IV) and (V) can be carried out under conditions of temperature and catalysis which are similar to those described above in connection with reactions (II) and (III).

As already mentioned, the cyclopolysiloxanes of the present invention find utility in many industrial and consumer oriented formulated products, either as a major component or as an additive. In the latter category, a particularly favored utility of these compounds is in skin care and hair care products, wherein they can impart a highly desirable "velvety" or "satin-like" feel to the respective substrate treated therewith. Skin care compositions of various forms are well known in the art and delivered in the form of solutions, emulsions, dispersions, lotions, gels, aerosols, solid stick products, ointments or creams. These compositions typically comprise at least one component selected from the group consisting of waxes, oils, humectants, fillers, emollients, pigments, sunscreens and various adjuvants, such as perfumes, fragrances and preservatives, inter alia. The use of conventional alkylmethyl siloxanes, particularly in combination with polydimethylsiloxane, is also known in this art (e.g., see U.S. Pat. No. 4,574,082 to Tietjen et al., hereby incorporated by reference to teach such cosmetic compositions). In such applications, the instant compounds offer improved latitude to the cosmetic formulator where a liquid product is desired.

Another preferred application of the cyclopolysiloxanes of the invention is in the area of hydraulic fluids, wherein the improved lubricity imparted by long alkyl chains is advantageously manifested in a composition having a fluid consistency over a wide temperature range.

EXAMPLES

The following examples are presented to further illustrate the compositions of this invention, but are not to be construed as limiting the invention, which is delineated in the appended claims. All parts and percentages in the examples are on a weight basis and all measurements were obtained at 25° C., unless indicated to the contrary.

EXAMPLE 1

Into a three-necked flask equipped with a thermometer, a condenser, stirrer and addition funnel there was charged 66.7 grams (0.50 mole) tetramethyldisiloxane and 1 gram of a 0.5% platinum-on-carbon catalyst (mesh size=8) which was predried at 150° C. for 4 hours. The contents were heated to reflux and a dropwise addition of 1-dodecene was initiated, whereupon the temperature increased slightly. After the hydrosilation reaction was completed, as evidenced by the dissipation of exothermal activity and analysis by gas chromatography, the excess disiloxane was removed by vacuum distillation. The resulting product consisted essentially of the confirmed structure HMe$_2$SiOSiMe$_2$(CH$_2$)$_{11}$CH$_3$ wherein Me hereinafter denotes a methyl radical.

EXAMPLE 2

A flask was charged with 11.1 grams (0.032 mole) of methylvinylcyclotetrasiloxane, 3.5 grams of hexane and 1 gram of the previously described platinum-on-carbon catalyst and this mixture was heated to the point of reflux, whereupon a dropwise addition of 42.8 grams (0.14 mole) of the compound obtained in Example 1 was initiated. The temperature climbed from about 95° C. to about 130° C. After completion of the reaction, the hexane solvent was removed by vacuum distillation to yield a clear, slightly amber liquid which was shown to have the following structure by field desorption mass spectrometry:

(MeSiO)$_4$
|
CH$_2$CH$_2$(Me$_2$)SiOSi(Me$_2$)—(CH$_2$)$_{11}$CH$_3$ and which had a density of 0.91 g/ml, a viscosity of 94 cS and a refractive index of 1.4497. This compound did not become waxy when cooled to −50° C. and was quite fluid at −10° C.

EXAMPLE 3

A procedure similar to that described in Example 1 was followed wherein tetramethyldisiloxane was reacted with 1-hexadecene to provide a compound having the structure HMe$_2$SiOSiMe$_2$(CH$_2$)$_{15}$CH$_3$

EXAMPLE 4

The compound produced in Example 3 was reacted with methylvinylcyclotetrasiloxane, as described in Example 2, to prepare a compound having the formula (MeSiO)$_4$
|
CH$_2$CH$_2$Me$_2$SiOSiMe$_2$(CH$_2$)$_{15}$CH$_3$ This product had a density of 0.89 g/ml, a viscosity of 87 cS.

EXAMPLE 5

A flask equipped with a thermometer, condenser, stirrer and addition funnel was charged with 46.6 grams (0.24 mole) of 1,13-tetradecadiene, 5 grams of hexane and 1 gram of platinum-on-carbon, described supra. The contents were heated to about 100° C. and 26.7 grams (0.12 mole) of a trisiloxane having the formula (Me$_3$SiO)$_2$SiMeH was added dropwise, during which the temperature rose to about 120° C. Upon completion of the reaction, unreacted olefin was removed by vacuum distillation to produce a product having the formula (Me$_3$SiO)$_2$Si(Me)—(CH$_2$)$_{12}$CH=CH$_2$

EXAMPLE 6

The compound prepared in Example 5 (35 grams; 0.084 mole) was charged to a flask equipped with a thermometer, stirrer, condenser and addition funnel along with 5 grams of hexane and 1 gram of platinum-on-carbon catalyst. The contents were heated to about 95° C. and 5.1 grams (0.021 mole) of methylhydrogencyclotetrasiloxane was added dropwise. The temperature peaked at about 115° C. and then subsided to about 105° C. upon completion of the reaction, at which point the clear, colorless product was decanted from the catalyst and the hexane was removed by vacuum distillation. The product consisted essentially of the structure (MeSiO)$_4$
|
(Me$_3$SiO)$_2$Si(Me)—(CH$_2$)$_{14}$— and had a density of 0.90 g/ml, a viscosity of 105 cS and a refractive index of 1.4502. This compound also did not become waxy when cooled to −50° C. and was also quite fluid at −10° C.

For comparison purposes, the cyclic siloxanes prepared above were contrasted with cyclic siloxanes of the prior art as to physical appearance, as shown in Table 1, wherein in each case the compound had the structure (QMeSiO)$_y$.

TABLE 1

| Group Q | Y | Physical Form |
|---|---|---|
| *Examples of the Invention:* | | |
| —CH$_2$CH$_2$(Me$_2$)SiOSi(Me$_2$)C$_{12}$H$_{25}$ | 4 | Fluid; viscosity = 94 cS @ 25° C. |
| —CH$_2$CH$_2$(Me$_2$)SiOSi(Me$_2$)C$_{16}$H$_{33}$ | 4 | Fluid; viscosity = 87 cS @ 25° C. |
| —(CH$_2$)$_{14}$—SiMe(Me$_3$SiO)$_2$ | 4 | Fluid; viscosity = 105 cS @ 25° C. |
| *Comparison Examples:* | | |
| —(CH$_2$)$_5$—CH$_3$ | 4 | Fluid; viscosity = 14 cS @ 25° C. |
| —(CH$_2$)$_7$—CH$_3$ | 4 | Fluid; viscosity = 21 cS @ 25° C. |
| —(CH$_2$)$_{11}$—CH$_3$ | 4 | Wax at 28° C. |
| —(CH$_2$)$_{13}$—CH$_3$ | 4 | Wax at 25° C. |
| —(CH$_2$)$_{17}$—CH$_3$ | 4 | Wax at 38° C. |
| —(CH$_2$)$_{19}$—CH$_3$ | 5 | Wax at 55° C. |
| —(CH$_2$)$_x$—CH$_3$ (x = 23 to 27) | 5 | Wax at 56° C. |

It can be seen from Table 1 that when long chain alkyl groups (i.e., those having more than about 12 carbon atoms) are attached to the silicon atoms of the above cyclopolysiloxanes, the compounds of the invention offer the advantage of reduced melt point and fluidity over comparable prior art cyclopolysiloxanes.

I claim:

1. A cyclopolysiloxane having the general structure

[—(R$_2$SiO)$_x$(R'QSiO)$_y$—]

wherein Q is a monovalent siloxane moiety selected from the group consisting of the structure (R$_3$SiO)$_2$SiR—A— and the structure GR$_2$SiOSiR$_2$—A'—, in which A is a divalent hydrocarbon group having 4 to 14 carbon atoms and A' is a divalent hydrocarbon group having 2 to 18 carbon atoms, each R' group and each G group is independently selected from the group consisting of an alkyl radical having 1 to 30 carbon atoms, a phenyl radical, an arylalkyl group and a halogenated alkyl radical having 3 to 6 carbon atoms, each R is independently selected from the group consisting of an alkyl radical having 1 to 30 carbon atoms, a phenyl radical, an arylalkyl group, a halogenated alkyl radical having 3 to 6 carbon atoms and hydrogen, and x and y are each integers with the proviso that (x+Y) is an integer having a value of 4 to 6 inclusive and y is at least 1.

2. The cyclopolysiloxane of claim 1 having the structure $$[(R'QSiO)_y]$$

wherein each R and R' is independently selected from alkyl radicals having 1 to 3 carbon atoms, Q is $(R_3SiO)_2SiR-A-$, in which A is a divalent hydrocarbon group having 4 to 14 carbon atoms, and y is 4, 5 or 6.

3. The cyclopolysiloxane of claim 2, wherein R' is a methyl radical.

4. The cyclopolysiloxane of claim 3, wherein R is a methyl radial.

5. The cyclopolysiloxane of claim 4, wherein group A is a linear alkylene group having 6 to 14 carbon atoms.

6. The cyclopolysiloxane of claim 5, wherein y is 4.

7. The cyclopolysiloxane of claim 1 having the structure $$[(R'QSiO)_y]$$

wherein each R and R' is independently selected from alkyl radicals having 1 to 3 carbon atoms, Q is $GR_2SiOSiR_2-A'-$, in which A' is a divalent hydrocarbon group having 2 to 18 carbon atoms and G is an alkyl radical having 1 to 30 carbon atoms, and y is 4, 5 or 6.

8. The cyclopolysiloxane of claim 7, wherein R' is a methyl radical.

9. The cyclopolysiloxane of claim 8, wherein R is a methyl radical.

10. The cyclopolysiloxane of claim 9, wherein group A' is a dimethylene group.

11. The cyclopolysiloxane of claim 10, wherein group G is an alkyl radical having 5 to 20 carbon atoms.

12. The cyclopolysiloxane of claim 11, wherein y is 4.

13. In a skin care composition comprising a cyclopolysiloxane, the improvement comprising using the cyclopolysiloxane of claim 1.

14. In a skin care composition comprising a cyclopolysiloxane, the improvement comprising using the cyclopolysiloxane of claim 2.

15. In a skin care composition comprising a cyclopolysiloxane, the improvement comprising using the cyclopolysiloxane of claim 7.

16. In a hair care composition comprising a cyclopolysiloxane, the improvement comprising using the cyclopolysiloxane of claim 1.

17. In a hair care composition comprising a cyclopolysiloxane, the improvement comprising using the cyclopolysiloxane of claim 2.

18. In a hair care composition comprising a cyclopolysiloxane, the improvement comprising using the cyclopolysiloxane of claim 7.

19. In a hydraulic fluid composition comprising a cyclopolysiloxane, the improvement comprising using the cyclopolysiloxane of claim 1.

20. In a hydraulic fluid composition comprising a cyclopolysiloxane, the improvement comprising using the cyclopolysiloxane of claim 2.

21. In a hydraulic fluid composition comprising a cyclopolysiloxane, the improvement comprising using the cyclopolysiloxane of claim 7.

* * * * *